United States Patent

Krill et al.

[11] Patent Number: 5,907,065
[45] Date of Patent: May 25, 1999

[54] METHOD OF PRODUCING β-ISOPHORONE BY THE ISOMERIZATION OF α-ISOPHORONE

[75] Inventors: Steffen Krill, Speyer, Germany; Günes Giray, Mavischir-Didim, Turkey; Frank Hübner, Ober-Ramstadt, Germany; Rainer Hahn, Karlstein, Germany; Klaus Huthmacher, Gelnhausen, Germany; Herbert Tanner, Hanau, Germany

[73] Assignee: Degussa Aktiengesellschaft, Frankfurt, Germany

[21] Appl. No.: 08/938,821

[22] Filed: Sep. 26, 1997

[30] Foreign Application Priority Data

Sep. 26, 1996 [DE] Germany .......................... 196 39 569

[51] Int. Cl.⁶ .................................................. C07C 45/67
[52] U.S. Cl. ........................... 568/341; 568/342; 568/366
[58] Field of Search ..................................... 568/341, 342, 568/366

[56] References Cited

U.S. PATENT DOCUMENTS 4,845,303  7/1989  Bellut et al. ............................. 568/341
5,276,197  1/1994  Nosberger et al. ..................... 568/341

FOREIGN PATENT DOCUMENTS 0 312 735  4/1989  European Pat. Off. .
0 488 045  6/1992  European Pat. Off. .
01 175954  7/1989  Japan .

Primary Examiner—Gary Geist
Assistant Examiner—Sreeni Padmanabhan
Attorney, Agent, or Firm—Pillsbury Madison & Sutro LLP

[57] ABSTRACT

A method of producing 3,5,5-trimethylcyclohexa-3-ene-1-one (β-isophorone) by isomerization of 3,5,5-trimethylcyclohexa-2-ene-1-one (α-isophorone) in a liquid phase in the presence of a homogeneous or heterogeneous catalyst in which a mixture with a relatively low concentration of β-isophorone is drawn off from the reaction container and the β-isophorone isolated by vacuum distillation. β-isophorone is an important synthetic structural element for the production of carotinoids, vitamins and pharmaceutical products.

28 Claims, No Drawings

METHOD OF PRODUCING β-ISOPHORONE BY THE ISOMERIZATION OF α-ISOPHORONE

CROSS-REFERENCE TO RELATED APPLICATION

This application claims priority from German Application No. 19639569.0, filed Sep. 26, 1996. The subject matter of which is hereby incorporated herein by reference.

FIELD OF THE INVENTION

The invention relates to a novel method of producing 3,5,5-trimethylcyclohexa-3-ene-1-one (β-isophorone) by the isomerization of 3,5,5-trimethylcyclohexa-2-ene-1-one (α-isophorone) in the liquid phase in the presence of a homogeneous or heterogeneous catalyst.

BACKGROUND OF THE INVENTION

β-isophorone has great economic significance since it is an important synthetic structural element for the production of carotinoids, vitamins and pharmaceutical products. In particular, β-isophorone is required as a precursor for ketoisophorone (2,6,6-trimethylcyclohex-2-ene-1,4-dione) and trimethylhydroquinone and therewith for the production of vitamin E. In addition, it is pivotably used in syntheses for odorous substances and natural compounds such as astaxanthine and abscisic acid and derivatives.

The production of isophorone is carried out by means of acetone trimerization under condensation of the $C_3$ structural elements. The primarily formed isomer is α-isophorone since it has, in contrast to the β isomer, a double bond conjugated to the keto function. For this reason the thermodynamic equilibrium is on the side of the α-isophorone; the β concentration is only approximately 1–2% and the adjustment of equilibrium takes place very slowly.

Although there are basically two different methods of preparation for arriving at ketoisophorone, namely, the direct oxidation of α-isophorone (α-IP)→ketoisophorone (KIP) and the indirect route via the isomerization α-isophorone→β-isophorone (β-IP) in a primary step and subsequent oxidation of the β-isophorone→ketoisophorone, the latter process is clearly advantageous. Scheme 1 presents these considerations for ketoisophorone synthesis in a clear manner.

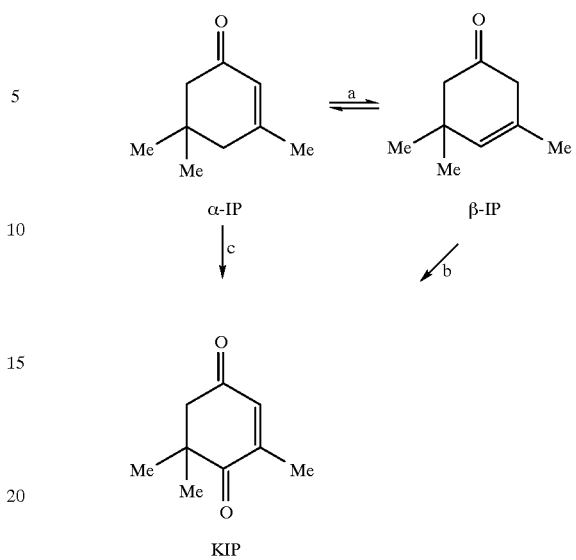

a = Isomerization of α-IP to β-IP
b = Oxidation of β-IP to KIP
c = Direct oxidation α-IP to KIP Numerous methods for the isomerization of α-IP have been described in the course of time which, however, have significant disadvantages. Viewpoints such as consumption of chemicals, poor space/time yields and problems in the workup have prevented, up to the present, a practical processing reaction on a large scale.

A number of publications are concerned with the isomerization in the liquid phase. The more pertinent state of the art is represented by the following publications:
D1=A. Heymes et al., Recherches 1971, 18, 104
D2=FR-A-1,446,246
D3=DE-OS-24 57 157
D4=U.S. Pat. No. 4,005,145
D5=EP-A-0,312,735
D6=JP 87-33019 corresp. to HEI-1-175954 of Jul. 12, 1989.

D1 discloses the isomerization of α-IP to β-IP with stoichiometric amounts of MeMgX (Me=methyl, X=halogen-) Grignard compound. 73% β-IP is obtained with evolution of methane in the presence of catalytic amounts of $FeCl_3$.

D2 relates to the isomerization of α-IP to β-IP in the presence of catalytic amounts of p-toluene sulfonic acid and generally aromatic sulfonic acids, especially aniline sulfonic acid. The amount of the catalyst used is 0.1–0.2 % relative to the α-IP used. However, a low degree of conversion and a high accumulation of byproducts prevent an industrial application of the method of D2.

According to D3, the preparation of β-IP takes place by means of boiling α-IP for several hours in triethanol amine, fractionation, washing the distillate with tartaric acid and sodium chloride solution. The consumption of chemicals is also considerable here.

In D4, acids with a pK=2–5 and a higher boiling point than β-IP (boiling point β-IP=186° C./760 mm Hg) are used as catalyst. The following are named:

Aliphatic and aromatic amino acids, adipic acid, p-methylbenzoic acid, 4-nitro-m-methylbenzoic acid, 4-hydroxybenzoic acid, 3,4,5-trimethoxybenzoic acid, vanillic acid, 4-trifluoromethylbenzoic acid, 3-hydroxy-4-nitrobenzoic acid and cyclohexane carboxylic acid and derivatives. The amount of catalyst used is 0.1–20 molar percent. The yield of β-IP (relative to α-IP used) is 74.5%.

At a rate of decrease of 11 ml/h β-IP and a simultaneous amount added of approximately 0.5 kg α-IP, the space-time yield and the production of β-IP is Y=0.218 kg β-IP/kg$_{cat}$/h and is thus too low to find industrial application. These values correspond to a space-time yield of Y$_{s-t}$=0.015 l$_{β-IP}$/h/l$_{solution}$.

A similar principle is followed in D5. Acetyl acetonates of transitional metals are used as π bond displacement catalysts. Even Al (acac) displays catalytic activity. The use of the catalyst takes place in 0.01–10% by weight related to the starting weight of α-IP. Metallic catalysts of groups IVb (Ti/Zr/Hf), Vb (V/Nb/Ta), VIb (Cr, Mo, W), VIIb (Mn/Tc/Re), the entire group VIII and aluminum are patented. The primarily obtained distillate has a β-IP content of 94%, a further Vigreux distillation enriches the β-IP content to 99%. This result corresponds, relative to amount of catalyst used and the time, to a yield of Y—9.4 liters β-IP per kilogram catalyst per hour. This corresponds, relative to the educt solution used, to a yield of Y$_{s-t}$=0.0376 l$_{β-IP}$/h/l$_{solution}$.

According to D6, the isomerization takes place in the liquid phase at temperatures around 200° C. Silica gels with or without the addition of alkyl-substituted imidazolines of the following formula are used as catalyst.

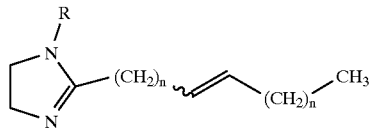

Typical experimental conditions: 300 g α-IP and 25.7 g SiO$_2$ are distilled 52 h in the presence of refined steel; 230 g β-IP (=76.6% yield) result with 99.9% purity. This result corresponds, relative to amount of catalyst used and the time, to a yield of Y=0.174 liters β-IP per liter catalyst per hour.

Moreover, the procedure described is unfavorable and the absolute production of β-IP low. The performance of isomerization and one-step distillation of the β-IP in one step is especially disadvantageous. It can be demonstrated that the re-isomerization of β-IP to α-IP occurs to a considerable extent on account of the high reaction temperature in the distillation apparatus.

SUMMARY OF THE INVENTION

In view of the state of the art cited and discussed herein, the invention has as its purpose avoiding the above-mentioned disadvantages of the previous methods and providing a method according to which 3,5,5-trimethylcyclohexa-3-ene-1-one can be produced from its isomer 3,5,5-trimethylcyclohexa-2-ene-1-one in a technically and industrially advantageous manner.

The method of the invention makes possible a high conversion rate and exceeds that of the methods previously known from the state of the art. Furthermore, the novel procedure reduces the accumulation of byproducts and improves the space time yield, relative to the volume of educt solution used.

The present invention relates to a method in which α-isophorone is reacted to form its isomer β-isophorone using a homogeneous or a heterogeneous catalyst in the liquid phase.

If the state of the art is followed, it is necessary to separate off the purest possible β-isophorone from the reaction container by distillation. However, under the known reaction conditions of isomerization a re-isomerization occurs in part at the boiling temperature of 186° C. so that the space-time yield as regards β-isophorone is heavily adversely impacted.

DETAILED DESCRIPTION OF THE INVENTION

It was now found that, contrary to this general view, it is more advantageous to draw off a mixture by distillation from the reaction container in which the isomerization takes place which mixture contains 0.5 to 75% by weight, especially 0.5 to 60% by weight and especially 0.5 to 40% by weight β-isophorone.

The coordination between the amount of β-isophorone being produced and the amount distilled off proves to be essential for an optimal planning of the separation rate.

It is advantageous if the rate of removal by distillation at the top of the reaction container approximately corresponds to the rate of formation of β-isophorone in the reaction container.

The method of the invention is carried out over a temperature range between 100 and <300° C. The temperature range between 150 and 260° C. is preferred.

The addition of a thinning agent or solvent is possible but not required.

The reaction is preferably carried out at a pressure of 10 mbar to 3 bar excess pressure. Quite especially favorable isomerization parameters are about 100 mbar to normal pressure (approximately 1 hPa) in combination with the boiling temperature of α-isophorone.

The method of the invention can be successfully operated in a continuous manner. The liquid phase containing the isomerizate is distilled under a vacuum after it has been separated off for the separating of α-isophorone and β-isophorone. The β-isophorone then accumulates with a purity>97%.

The final distillation takes place, in contrast to the state of the art, at temperatures at which the temperature dependent re-isomerization is largely excluded.

It has proved to be advantageous thereby to recycle the bottom product of the final distillation into the isomerization stage.

As a result of this procedure, which is distinguished from the state of the art, in which procedure a β-isophorone with the highest possible percentage yield is drawn off directly out of the reaction container, a higher space-time yield, relative to the volume of the educt solution, as well as a higher yield, relative to the amount of catalyst, of β-isophorone per kg of catalyst used, is obtained.

All heterogeneous catalysts known from the state of the art are suitable as catalysts.

The isomerization can also take place thereby, if necessary, in the presence of an organic base.

By way of example, oxides or mixed oxides of an element of the groups IIa, VIII, Ib, IIIa and Va of the periodic system of elements or also salts of said elements such as, in particular, carbonates or halides as well as SiO$_2$, which salts are insoluble under test conditions, are used as heterogeneous catalysts in the sense of the invention. The group division of the main and secondary groups of the periodic system of elements takes place according to the designation in accordance with IUPAC, Pure and Appl. Chem., 66, 2423–2444, 1994. Thus, the metals Be, Mg, Ca, Sr and Ba belong to group IIa; the metals Fe, Co, Ni, Ru, Rh, Pd, Os, Ir and Pt to group VIII; and the elements Cu, Ag, Au, B, Al, Ga, In, Tl, N, P, As, Sb and Bi to the groups Ib, IIIa and Va.

The compounds which can be used in accordance with the invention as heterogeneous catalysts include the oxides or mixed oxides of the above-named elements. The term mixed oxides signifies a compound in this connection in which oxygen forms a compound with more than one of the cited elements.

The oxides which can be used within the scope of the invention include BeO, MgO, CaO, SrO, BaO, $TiO_2$, $ZrO_2$, $MoO_3$, $Fe_3O_4$, $Fe_2O_3$, CoO, $Co_3O_4$, NiO, $PdO_2$, $PtO_2$, ZnO, $Al_2O_3$, $SiO_2$, silica gel.

The mixed oxides which can be used within the scope of the invention also include, in addition to mixed compounds of the oxides cited above, in particular $Al_2O_3/SiO_2$ and zeolites of various types, e.g. H-ZSM-5.

Of the oxides or mixed oxides indicated above those are preferred in particular which contain an element of the groups IIa, IIIa or VIII of the periodic system or $SiO_2$.

Oxides or mixed oxides of calcium and/or magnesium are used with special preference within the scope of the invention.

In a further embodiment of the method of the invention it is preferred that an oxide or mixed oxide of cobalt and/or nickel is used.

Quite especially preferred oxides are, among others, $Co_3O_4$ as well as MgO and CaO.

Another catalyst which is especially preferred is $\gamma$-$Al_2O_3$.

Cobalt carbonates and nickel carbonates, optionally in their hydrate form, are especially suitable.

In addition to the use of oxides or mixed oxides as heterogeneous catalysts in accordance with the invention for the isomerization of $\alpha$-isophorone to $\beta$-isophorone, even oxides and mixed oxides of the groups IIa, VIII, Ib, IIIa and Va of the periodic system of elements as well as $SiO_2$ doped with elementary metals can be used with good success. Elements, especially metals, from the same groups of the periodic system can be used for the doping. The doping metals to be preferably used include, among others, the metals of groups VIII and IIa. In a special variation the method of the invention is characterized in that a catalyst is used which is doped with a metal from group VIII of the periodic system. Within group VIII the metals cobalt and/or nickel are especially favorable as doping metals.

The amount of the metal used for doping is not especially critical and can therefore be varied over a broad range. It is preferred that the doping metal is used in an amount of 0.1 to 60% by weight (wt/wt) relative to the oxide or mixed oxide. An especially favorable catalyst is obtained if a $\gamma$-$Al_2O_3$ or $Co_3O_4$ doped with nickel and/or cobalt is used.

Furthermore, the catalyst or also the catalyst doped with a metal can be present in pure form or fixed on a carrier material or mixed with the carrier, which carrier material can be one of the described catalysts. Other carrier materials are known to the one skilled in the art. They include carriers such as $\alpha$-$Al_2O_3$, $\gamma$-$Al_2O_3$, $SiO_2$, $SiO_2/Al_2O_3$ of different modules, aluminum salts such as e.g. aluminum silicates and aluminum phosphates, activated carbon, etc.

Even the amount of the catalyst to be used for the isomerization can basically be varied over a rather large range. It is preferred that the catalyst is used in a ratio between 0.01 and 50% by weight (wt/wt) relative to $\alpha$-isophorone. In an especially preferred variant of an embodiment, the method of the invention is characterized in that the catalyst is used in a ratio of between 0.2 and 10% by weight (wt/wt) relative to $\alpha$-isophorone.

In yet another especially preferred embodiment the ratio of catalyst to $\alpha$-isophorone is in a range between 0.5 and 5% by weight (wt/wt).

However, the method of the invention is not limited to a heterogeneously catalyzed reaction. Even a homogeneously catalyzed isomerization is comprehended by the procedure of the invention.

The conditions for the reaction are such that the homogeneous catalysts used therefore are known from the state of the art.

The following should be explicitly named once again:

Acetylacetonates of transitional metals (IUPAC classification) of the groups IVb, Vb, VIb, VIIb and VIII as well as aluminum (from DE-OS 37 35 211= EP-A-0,312,735).

Brønsted acids which are stable under the thermal reaction conditions and have a pK value of 2–5. They include, e.g., p-toluene sulfonic acids and various substituted derivatives (see Belgian patent 826,113), generally aromatic sulfonic acid.

Organic acids with a pK of 2–5 (from U.S. Pat. No. 4,005,145):

Monocyclic, aromatic or alicyclically substituted mono-, di- or oligocarboxylic acids, e.g. adipic acid, p-methyl benzoic acid, 4-nitro-m-methyl benzoic acid, 4-hydroxybenzoic acid, 3,4,5-trimethoxybenzoic acid, vanillic acid, 4-trifluoromethylbenzoic acid, 3-hydroxy-4-nitrobenzoic acid and cyclohexane carboxylic acid and derivatives.

The homogeneous catalyst is preferably used in a weight percentage of 0.1 to 5, especially 0.1 to 1% by weight relative to the $\alpha$-isophorone.

EXAMPLE 1

Commercial $Co_3O_4$ of the Merck Company (Co(II/III) oxide) is used. The form of catalyst used is powdery in this instance but a granulated form is also catalytically active. A pretreatment of the catalyst is not necessary. The apparatus for carrying out the isomerization consists of a closed-circuit heater heated with two electrically supplied rod inserts. 700 ml industrial $\alpha$-isophorone is placed in a receiver (Atochem company>98%) and 25 g $Co_3O_4$ added. A distillation column 1.2 m long and with an inside diameter of 25 mm filled with V4A Raschig rings of 4 mm Ø rests above the closed-circuit heater. The suspension is heated at normal pressure up to boiling temperature and the amounts of the $\alpha$-IP supplied via a Telab pump and of the distillate taken off are coordinated with one another. The following $\beta$-IP content is adjusted in the primary distillate as a function of the rate of distillate taken off.

| Rate of taking off distillate | 20 ml/h | 40 ml/h | 80 ml/h | 120 ml/h | 160 ml/h | 260 ml/h |
|---|---|---|---|---|---|---|
| $\beta$-IP content (ml) | 47.3 | 44.4 | 38.9 | 33.6 | 26.8 | 19.0 |
| Production of $\beta$-IP/h(ml/h) | 9.4 | 17.7 | 31.1 | 40.4 | 43.5 | 49.5 |

The bottom temperature of the isomerization remains constant during the reaction period at 216–217° C. The accumulating primary distillate is delivered to a distillation column operating at a vacuum of 5 mbar–100 mbar. The top product accumulating at 12 mbar has a boiling point of 55–58° C. and consists of >97% of $\beta$-isophorone. At the described conditions of the example, 50 g $\beta$-isophorone is produced per hour. The $\alpha$-isophorone non-reacted as bottom product is returned, with a residual $\beta$-IP content<3%, to the isomerization unit. The selectivity relative to the conversion is >98%. The yield relative to the amount of catalyst used is $Y=1.98\ l_{\beta-IP}/h/kg_{cat}$. The space time yield ($Y_{s-t}$ to the volume of the solution to be isomerized is $Y_{s-t}=0.0707\ l_{\beta-IP}/h/l_{solution}$.

EXAMPLE 2

25 g of a magnesium oxide catalyst is filled into the apparatus already described. A primary distillate with the following composition is taken off using the same continuous method of operation (see Example 1) at the top of the isomerization unit in accordance with the rate of taking off the distillate:

| Rate of taking off distillate | 40 ml/h | 120 ml/h | 240 ml/h |
|---|---|---|---|
| β-IP content (ml) | 46.0 | 34.8 | 21.5 |
| Production of β-IP (ml/h) | 18.4 | 41.8 | 51.6 |

The absolutely produced amount of β-IP can be optimized by further raising the rate of taking off the distillate. The bottom temperature of the isomerization is constantly 216–217° C. for the time of the reaction. The yield relative to the amount of catalyst used is $Y=2.064\ l_{\beta-IP}/h/kg_{cat}$. The space time yield relative to the educt solution used is $Y_{s-t}=0.0737\ l_{\beta-IP}/h/l_{solution}$.

EXAMPLE 3

1.160l α-IP are reacted on 4.4 g $Co_3O_4$ catalyst (cobalt black $Co_3O_4$; MW=240.8 g/mol; 4.4 g=18.3 mmol) (IP= 138.21 g/mol; 1/160 ml=8.393 mmol) in the described apparatus (same conditions of isomerization as Example 1). Primary distillates with the following β-IP content are obtained as a function of the rate of taking off the distillate:

| Rate of taking off distillate | 20 ml/h | 40 ml/h | 80 ml/h | 160 ml/h | 240 ml/h | 280 ml/h |
|---|---|---|---|---|---|---|
| β-IP content (ml) | 52.6 | 47.3 | 40.4 | 25.9 | 16.6 | 14.7 |
| Production of β-IP/h(ml/h) | 10.5 | 18.9 | 32.2 | 41.4 | 39.8 | 41.2 |

The bottom temperature of the isomerization unit is a constant 216–217° C. The yield relative to the amount of catalyst used is $Y=9.363\ l_{\beta-IP}/h/kg_{cat}$. The space time yield relative to the educt solution used is $Y_{s-t}=0.0588\ l_{\beta-IP}/h/l_{solution}$.

EXAMPLE 4

Instead of the cobalt oxide catalyst of example 3 α-aluminum oxide (Hoffmann La Roche Co. A2) is added in the isomerization unit. The reaction is carried out similarly to Example 1. α-IP/β-IP mixtures of the following composition are obtained with a continuous removal of distillate:

| Rate of taking off distillate | 20 ml/h | 40 ml/h | 95 ml/h | 160 ml/h | 180 ml/h |
|---|---|---|---|---|---|
| β-IP content (ml) | 58.4 | 34.5 | 17.6 | 12.2 | 9.7 |
| Production of β-IP/h (ml/h) | 11.7 | 13.8 | 16.7 | 19.5 | 17.5 |

The isomerization is carried out at a constant bottom temperature of 216–217° C. The yield relative to the amount of catalyst used is $Y=0.78\ l_{\beta-IP}/h/kg_{cat}$. The space time yield relative to the educt solution used in $Y_{s-t}=0.0278\ l_{\beta-IP}/h/l_{solution}$.

EXAMPLE 5

$Co_3O_4$ (Merck Company) is used without pretreatment as catalyst. The dimensioning of the apparatus corresponds to that of the previous examples, the stoichiometric ratios of catalyst/α-IP correspond to the conditions of Example 1. The pressure and temperature of the isomerization are varied and the β-IP content of the primary distillate accumulating at the top of the column is determined at a constant rate of taking off the distillate of 120 ml/h. The isomerization temperatures associated with the corresponding pressures can be seen from the table.

| Temperature bottom (° C.) | Pressure (mbar) | β-IP content (liquid %) |
|---|---|---|
| 216 | 1000 | 33.8 |
| 203 | 770 | 25.8 |
| 192 | 580 | 18.6 |
| 178 | 390 | 14.6 |

EXAMPLE 6

The apparatus described in Examples 1–5 is operated semi-continuously (non-reacted α-IP is not brought into contact with the catalyst again) and the isomerization unit filled with 25 g $Co_3O_4$ (Merck Company). Then, a total of 11 l industrial α-IP are continuously charged with a Telab laboratory pump during which an approximately 20% by liquid volume β-IP/α-IP mixture accumulates as primary distillate. The bottom temperature of the isomerization unit remains a constant 216–217° C. during the reaction time. The rate of removal of distillate is about 250 ml/h, which corresponds to a production of β-IP of 50 ml β-IP/h. 905 g of a thin oil remain as bottom product, 117 g (12.9%) of which consists of overcondensates and 87.1% of which consists of recoverable α-IP. The accumulation of byproduct relative to α-IP reacted is thus 5.3%.

EXAMPLE 7

The apparatus described in Examples 1–5 is operated continuously. The isomerization unit is connected to the distillation column via a Telab pump. The α-IP accumulating in the bottom of the distillation unit is taken off via an overflow container and returned to the isomerization. A β-isophorone with a purity>97 % is taken off at the top of the distillation column. 3.7 l α-IP (Atochem: >98% GC) are converted in this manner. 25 g cobalt black (Merck Company) is used as catalyst, the rate of decrease is 240–250 ml/h and the isomerization temperature is 216–217° C. The primary mixture has a β-IP content of 20–22%. During the reaction period, the catalyst shows no aging and can be almost completely recovered at the end of the reaction by filtration (23.3 g $Co_3O_4$). After the end of the reaction 555 g α-IP and 60 g high boiling fraction remain in the forced-circulation reboiler, which can be readily separated by distillation. 3.07 kg β-IP (purity~98%) are obtained as distillate. The yield relative to the conversion is thus 97.6%. The accumulation of byproduct is 1.9%. The remainder consists of water which is produced by α-IP dimerization or condensation, or which passes through by means of the industrial educt into the reaction.

EXAMPLE 8

50 g CaO are added as catalyst into a 2-l three-neck flask with KPG agitator and 120 cm Vigreux column set on top and 1.5 l α-isophorone placed in the flask. The pressure of the apparatus is lowered to 350 mbar, during which the liquid begins to boil at an inside temperature of 175–180° C. The three-neck flask is additionally equipped with a dropping funnel which permits a continuous adding of α-IP. The addition of fresh α-IP corresponds to the amount of α-IP/β-IP mixture taken off at the top of the Vigreux column. 200 ml isomeric mixture is continuously taken off, the β content of which is approximately 21–22% by weight. The mixture being produced is distilled in a vacuum, the α-IP accumulating in the bottom of the pure distillation is returned to the catalyst. β-IP product with a purity>98% can be taken off at the top of the pure distillation. 3 kg α-IP are reacted with the procedure, yielding 2,850 g of a>98% β-IP product. The selectivity, relative to reacted α-IP, is >95%. The catalyst is still active after regeneration by filtration and washing with α-IP and can be used for another cycle. The yield relative to the amount of catalyst used is $Y=0.88\ l_{\beta\text{-}IP}/h/kg_{cat}$. The space-time yield relative to the educt solution used is $Y_{s\text{-}t}=0.0293\ l_{\beta\text{-}IP}/h/l_{solution}$.

EXAMPLE 9

The apparatus described in Examples 1 to 6 is operated discontinuously. 25 g silica gel 60 (Merck 7734) is used as catalyst, the isomerization distillation boiler is filled with 300 g (=325 ml) α-isophorone. An α-IP/β-IP mixture with the following composition accumulates at the top of the isomerization unit as a function of the rate of removal of distillate:

| Rate of taking off distillate | 80 ml/h | 120 ml/h | 220 ml/h |
|---|---|---|---|
| β-IP content (ml) | 37.5 | 22.8 | 13.1 |
| Production of β-IP (ml/h) | 30 | 27.36 | 28.8 |

The reaction is carried out at normal pressure and temperatures of 216–217° C. bottom temperature. In the test arrangement presented above the yield relative to amount of catalyst used is $Y=1.2\ l_{\beta\text{-}IP}/h/kg_{cat}$. The space-time yield relative to the educt solution used is $Y_{s\text{-}t}=0.0923\ l_{\beta\text{-}IP}/h/l_{solution}$.

If the procedure described in Japanese Offenlegungsschrift (A) HEI 1-175954 is followed (300 g α-IP; 25.7 g SiO$_2$, rate of taking off distillate 5 g/h) and an 89% β-IP/α-IP mixture/h is drawn off using SiO$_2$ as catalyst, the yield relative to the amount of catalyst is $Y=0.174\ kg_{\beta\text{-}IP}/h/kg_{cat}$. The space time yield relative to the educt solution used is $Y_{s\text{-}t}=0.0149\ l_{\beta\text{-}IP}/h/l_{solution}$.

EXAMPLE 10

The same apparatus as is described in Example 9 is used and 5% by weight CoCO$_3$ (cobalt carbonate, AMG Kokkola Company) used as catalyst. The formation rate of β-IP is 67 g/h/l at a rate of decrease of 25% by vol. of the α-IP mixture used. A selectivity of S=98% is determined by quantification of the high-boiler portion produced.

What is claimed is:

1. A method of producing 3,5,5-trimethylcyclohexa-3-ene-1-one (β-isophorone) by isomerization of 3,5,5-trimethylcyclohexa-2-ene-1-one (α-isophorone) in a reaction mixture in presence of a catalyst, comprising:
   drawing off a mixture by distillation out of the reaction mixture during isomerization, which mixture comprises 0.5 to 75% by weight β-isophorone; and
   isolating the β-isophorone by vacuum distillation.

2. The method according to claim 1 wherein the isomerization is conducted in the presence of a heterogeneous catalyst.

3. The method according to claim 1, wherein the isomerization is homogeneously catalyzed.

4. The method according to claim 1, wherein the mixture comprises 0.5 to 60% by weight β-isophorone.

5. The method according to claim 1, wherein the mixture comprises 0.5 to 40% by weight β-isophorone.

6. The method according to claim 1, wherein a bottom portion is returned from the vacuum distillation into the catalyzed isomerization step.

7. The method according to claim 1, wherein the method is carried out continuously.

8. The method according to claim 2, wherein the catalyst comprises a member selected from the group consisting of an oxide or mixed oxide of an element of the groups IIa, VIII, Ib, IIIa and Va of the periodic system, salts of said elements which salts are insoluble under test conditions, SiO$_2$ and silica gel, and the isomerization is optionally carried out with the addition of an organic base.

9. The method according to claim 2, wherein the catalyst comprises an oxide or mixed oxide of an element of the groups IIa and VIII of the periodic system.

10. The method according to claim 9, wherein the catalyst comprises an oxide or mixed oxide of Ca and/or Mg.

11. The method according to claim 9, wherein the catalyst comprises an oxide or mixed oxide of Co and/or Ni.

12. The method according to claim 9, wherein the catalyst comprises Co$_3$O$_4$.

13. The method according to claim 1 wherein the catalyst is doped with a metal from group VIII of the periodic system.

14. The method according to claim 13, wherein the catalyst is doped with Ni and/or Co.

15. The method according to claim 13, wherein the doping metal is used in an amount of 0.1–60% by weight (wt/wt) relative to the oxide or mixed oxide.

16. The method according to claim 13, wherein the catalyst comprises γ-Al$_2$O$_3$ or Co$_3$O, doped with Ni and/or Co.

17. The method according to claim 3, wherein the catalyst comprises a member selected from the group consisting of acetylacetonates of transitional metals of groups IVb, Vb, VIb and VIII and acetylacetonates of aluminum.

18. The method according to claim 1, wherein the catalyst comprises between 0.01 and 50% by weight (wt/wt) relative to α-isophorone.

19. The method according to claim 15, wherein the catalyst comprises between 0.2 and 10% by weight (wt/wt) relative to α-isophorone.

20. The method according to claim 16, wherein the catalyst comprises between 0.5 and 5% by weight (wt/wt) relative to α-isophorone.

21. The method according to claim 3, wherein the catalyst comprises 0.1 to 1% by weight relative to the α-isophorone.

22. The method according to claim 1 wherein the isomerization is carried out at temperatures between 100 and <300° C., during which the pressure is set so that the reaction takes place in the liquid phase.

23. The method according to claim 22, wherein the isomerization is carried out at normal pressure of approximately 1 hPa and at the boiling temperature of α-isophorone.

24. The method according to claim 7, wherein the isomerization is carried out at a temperature of 130 to 250° C. and a pressure of 1000 to 1.5×10$^5$ Pa, reaction mixture is continuously drawn off and distilled at a pressure of 100 to $3 \times 10^4$ Pa and distillation bottom is optionally returned into the isomerization.

25. The method according to claim 1 wherein the isomerization is carried out at a temperature between 150–260° C., during which the pressure is set so that the reaction takes place in the liquid phase.

26. A method of producing 3,5,5-trimethylcyclohexa-3-ene-1-one (β-isophorone) by isomerization of 3,5,5-trimethylcyclohexa-2-ene-1-one (α-isophorone) in a reaction mixture in presence of a Bronsted acid homogeneous catalyst having a pK value of 2–5, comprising:

drawing off a mixture by distillation out of the reaction mixture during isomerization, which mixture comprises 0.5 to 75% by weight β-isophorone; and isolating the β-isophorone by vacuum distillation.

27. A method of producing 3,5,5-trimethylcyclohexa-3-ene-1-one (β-isophorone) by isomerization of 3,5,5-trimethylcyclohexa-2-ene-1-one (α-isophorone) in a reaction mixture in presence of a heterogeneous catalyst selected from the group consisting of:

a carbonate or halide of an oxide or mixed oxide of an element of the groups IIa, VIII, Ib, IIIa and Va of the periodic system, and the isomerization is optionally carried out with the addition of an organic base, comprising:

drawing off a mixture by distillation out of the reaction mixture during isomerization, which mixture comprises 0.5 to 75% by weight β-isophorone; and isolating the β-isophorone by vacuum distillation.

28. The method according to claim 27, wherein the catalyst comprises a cobalt carbonate or nickel carbonate, optionally in a hydrate form.

* * * * *